United States Patent
Gertz et al.

(10) Patent No.: US 10,006,870 B2
(45) Date of Patent: Jun. 26, 2018

(54) MICROPATTERNING TECHNIQUE FOR CREATING MORPHOLOGICALLY SPECIFIC FREE-FLOATING STRUCTURES FOR USE AS STANDARDS IN THE PHARMACEUTICAL INDUSTRY

(71) Applicant: ZebraSci, Inc, Temecula, CA (US)

(72) Inventors: Frederick Talley Gertz, Riverside, CA (US); Robert James Schultheis, Temecula, CA (US)

(73) Assignee: ZebraSci, Inc, Temecula, CA (US)

( * ) Notice: Subject to any disclaimer, the term of this patent is extended or adjusted under 35 U.S.C. 154(b) by 0 days. days.

(21) Appl. No.: 15/444,509

(22) Filed: Feb. 28, 2017

(65) Prior Publication Data

US 2017/0254759 A1    Sep. 7, 2017

Related U.S. Application Data

(60) Provisional application No. 62/304,578, filed on Mar. 7, 2016.

(51) Int. Cl.
*G01N 21/90* (2006.01)
*A61J 1/14* (2006.01)
(Continued)

(52) U.S. Cl.
CPC .......... *G01N 21/90* (2013.01); *A61J 1/1468* (2015.05); *B05D 3/067* (2013.01); *B05D 3/107* (2013.01);
(Continued)

(58) Field of Classification Search
CPC ....... A61J 1/1468; B05D 3/067; B05D 3/107; G01N 15/0205; G01N 15/14; G01N 2015/0053; G01N 2015/0294
See application file for complete search history.

(56) References Cited

U.S. PATENT DOCUMENTS 9,418,416 B2    8/2016  Milne
9,842,408 B2 *  12/2017 Milne ....................... G06T 7/60
(Continued)

OTHER PUBLICATIONS

DeGrazio et al. The Glass Quandary. IPQ in the News, IPQ Publications LLC, Aug. 7, 2011. http://www.contractpharma.com/issues/2012-01/view_features/the-glass-quandary#sthash.0j3mkgRd.dpuf.
(Continued)

*Primary Examiner* — Seahvosh Nikmanesh
(74) *Attorney, Agent, or Firm* — Lumen Patent Firm

(57) ABSTRACT

A method is provided of using morphologically specific free-floating structures as Standards in the pharmaceutical industry to test objects in drug containers. These structures are micropatterned according to a desired pattern. A container is filled with a defined number of the standards, which then can be used as a standard reference for testing other drug products held in a drug container. The testing pertains to optically identifying structures in the drug container that can be similar in size and shape as the standards, or that can be different in size and shape as the standards. The advantage of the method is that imaging systems with tracking algorithms that count and track sub-visible and visible particles in solution can be used to identify e.g. glass flakes and other foreign particles by comparing them to the shape and size of the standard reference particles.

3 Claims, 4 Drawing Sheets

(51) Int. Cl.
  *G01N 15/14* (2006.01)
  *G01N 15/02* (2006.01)
  *B05D 3/06* (2006.01)
  *B05D 3/10* (2006.01)
  *G01N 15/00* (2006.01)

(52) U.S. Cl.
  CPC ......... *G01N 15/0205* (2013.01); *G01N 15/14* (2013.01); *G01N 2015/0053* (2013.01); *G01N 2015/0294* (2013.01); *G01N 2201/13* (2013.01)

(56) References Cited

U.S. PATENT DOCUMENTS

| | | | |
|---|---|---|---|
| 9,892,523 B2* | 2/2018 | Milne | G06T 7/60 |
| 2014/0268123 A1* | 9/2014 | Juvinall | G01N 21/9081 356/239.4 |

OTHER PUBLICATIONS

Wen et al. Nondestructive Detection of Glass Vial Inner Surface Morphology with Differential Inteference Contrast Microscopy. J. Phillips, Journal of Pharmaceutical Sciences, 101, 1378-1384 (2012).

Mitigating Risks Associated with Auto-Injector Applications, 5th Int. Conf. and Exhib. Pharmaceutics and Novel Drug Delivery Systems, Schultheis, Mar. 16-18, 2015 Crowne Plaza, Dubai, UAE. https://vimeo.com/198453736.

Makwana et al. Prefilled syringes: An innovation in parenteral packaging. Int. J. Pharm. Investig. Oct.-Dec.; 1(4): 200-206 (2011).

* cited by examiner

MICROPATTERNING TECHNIQUE FOR CREATING MORPHOLOGICALLY SPECIFIC FREE-FLOATING STRUCTURES FOR USE AS STANDARDS IN THE PHARMACEUTICAL INDUSTRY

CROSS-REFERENCE TO RELATED APPLICATIONS

This application claims priority from U.S. Provisional Patent Application 62/304,578 filed Mar. 7, 2016, which is incorporated herein by reference.

FIELD OF THE INVENTION

The invention relates to micropatterning techniques for creating free-floating structures for use as standards in the pharmaceutical industry.

BACKGROUND OF THE INVENTION

In parenteral packaging of medicine that is taken into the body or administered in a manner other than through the digestive tract, as by intravenous or intramuscular injection, glass is the most common material used for storage of drug products. Glass, especially type I borosilicate glass, is desirable for its strength, resistance to temperature variation, and general biological and chemical compatibility. With the advent of superior visual inspection methods there has been an increase in reports of small particles found within drug vials.

One example of great concern within the pharmaceutical community is the issue of glass delamination. Glass delamination is the sudden appearance of glass flakes or lamellae found within drug packaging that appear to have originated from the vial itself. In these cases the drug product reacts with the glass and causes some breakage into the drug solution.

Some tools have been developed to allow for the detection of glass flakes within a vial, but to date well-defined metrological tools are still lacking. Currently the community tends to utilize glass microspheres available from the National Institute of Standards and Technology (NIST, Gaithersburg, Md.), to simulate glass flakes, but these can be inadequate as they lack the morphology, and unique optical characteristics of a flake. Current particle standards are available with either a known size or defined number/concentration of particles, but not both parameters.

The present invention pertains to at least a process to create standard structures or samples with similar chemical, morphological and dimensional characteristics of actual glass flakes as seen in drug products. The aim is to advance the art and utilize these standards with detection and drug characterization equipment to determine the capability of detecting glass flakes.

SUMMARY OF THE INVENTION

The present invention provides a micropatterning method for creating morphologically specific free-floating structures to be used as Standards in the pharmaceutical industry to test surface delamination of drug containers. In this embodiment, these structures will have similar characteristics to free-floating structures as in a drug product caused by surface delamination of containers holding the drug product.

The micropatterning technique creating the structures defines the following steps. First a substrate is provided. A layer of an UV light sensitive material is deposited onto the substrate. The wafer is exposed to UV light underneath a photomask with a desired pattern and specific morphologic dimensions defined by the desired pattern to remove the areas exposed to the UV light and leaving the desired pattern of the UV light material on the substrate. The substrate as well as the desired pattern of the UV light material left on the substrate is coated with a coating layer. The thickness of the coating does not exceed the thickness of the UV light sensitive layer. A solvent is then used to lift-off the structures of the coating layer, which are defined by the desired pattern. The lifted-off structures are referred to as standards.

A container is provided which is filled a defined number of the standards. The filled container is then ready to be used as a standard reference for testing other drug products held in a drug container. Such a drug container can be made out of a material similar to the coating layer, or such a drug container can have an inner coating similar to the coating layer. The testing pertains to optically identifying structures in the drug container that can be similar in size and shape as the standards, or that can be different in size and shape as the standards.

The present invention further provides a micropatterning method for creating morphologically specific free-floating structures for use as Standards in the pharmaceutical industry to test objects in drug containers. In this embodiment, these structures are micropatterned according to the same method as defined supra. Further in this embodiment, a container is provided which is filled a defined number of the standards. The filled container is then ready to be used as a standard reference for testing other drug products held in a drug container. The testing pertains to optically identifying structures in the drug container that can be similar in size and shape as the standards, or that can be different in size and shape as the standards.

The present invention further provides a method of using morphologically specific free-floating structures as Standards in the pharmaceutical industry to test objects in drug containers. These structures are micropatterned according to a desired pattern. Further in this embodiment, a container is provided which is filled a defined number of the standards. The filled container is then ready to be used as a standard reference for testing other drug products held in a drug container. The testing pertains to optically identifying structures in the drug container that can be similar in size and shape as the standards, or that can be different in size and shape as the standards.

Embodiments of the invention pertain to foreign object in the drug that could come from delamination or the inner surface as well as foreign objects that come from other parts of the drug container or have come with the drug in the filling process. For example, metal particles may be present because the robot that filled the drug container may have had a malfunction that allowed the filling to proceed while distributing pieces of metal along with the drug. In this case, the comparison in the testing would identify the shape of the foreign (metal) particles. Other foreign objects could be rubber pieces that have come off a plunger, if used, which could come off the plunger if the prefilled syringe has been stored for some time.

The advantage of the invention is that various imaging systems (ZebraSci Inc, Temecula, Calif.) with tracking algorithms that count and track sub-visible and visible particles in solution can be used to identify glass flakes and other foreign particles by comparing them to the shape and size of the standard reference particles. The appearance of glass flakes in solution indicates that there is significant damage to the primary container's internal surfaces and this may lead to product recalls as it is a serious safety issue. The use of standard reference particles is also important to prevent the tracking algorithms from being fooled by small air particles and by particle and surface defects on the primary container.

DETAILED DESCRIPTION

Figure 1:
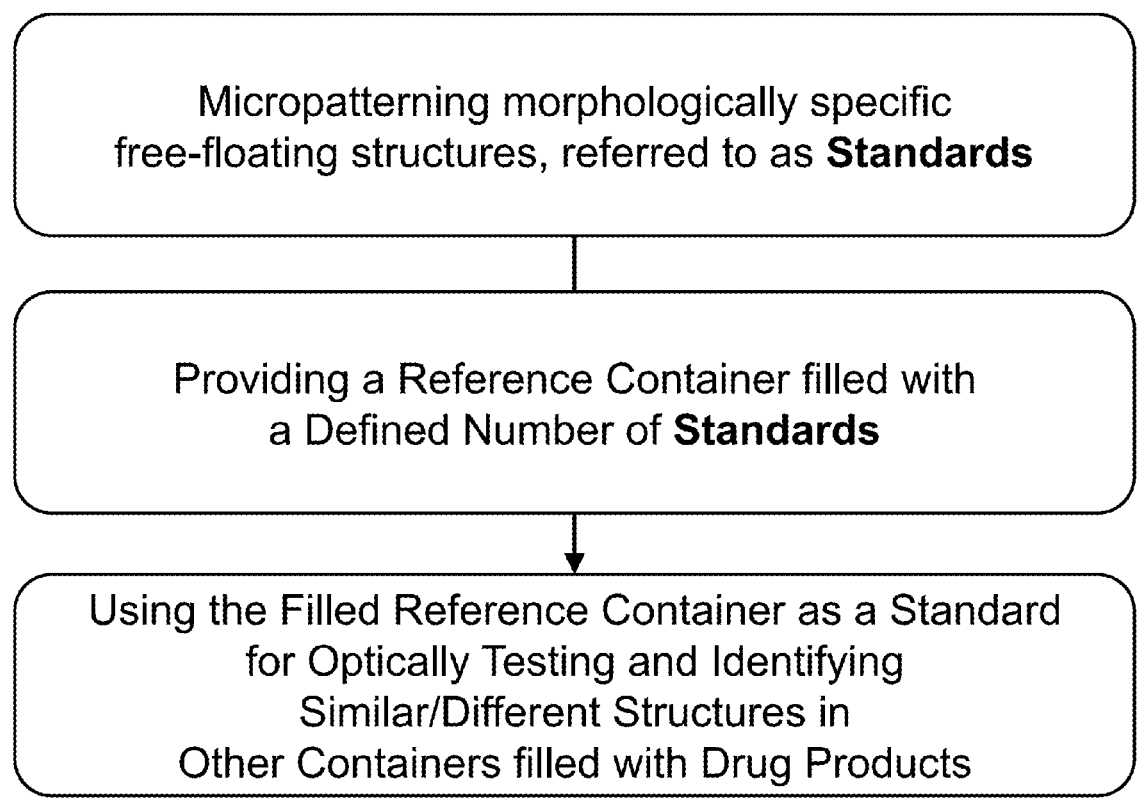
FIG. 1 shows a method according to an exemplary embodiment of the invention.
Figure 2A:
FIGS. 2A-E show according to an exemplary embodiment of the invention a graphical depiction of the method required to create Standard samples.
Figure 2B:
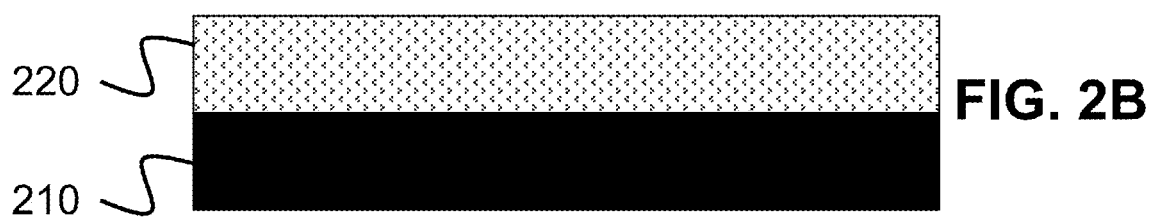
Figure 2C:
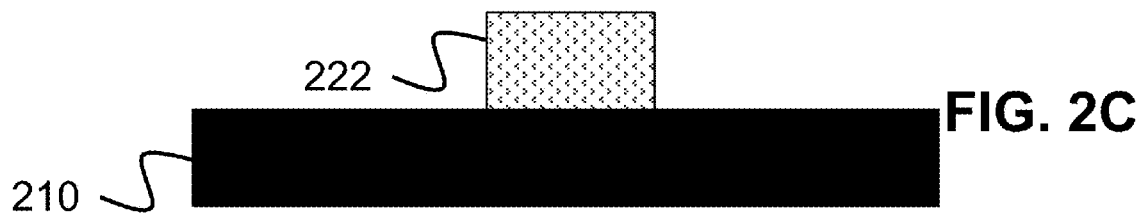
Figure 2D:
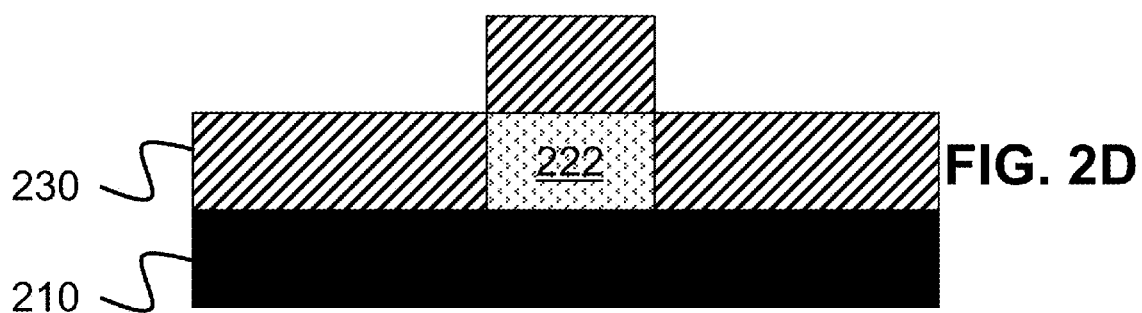
Figure 2E:
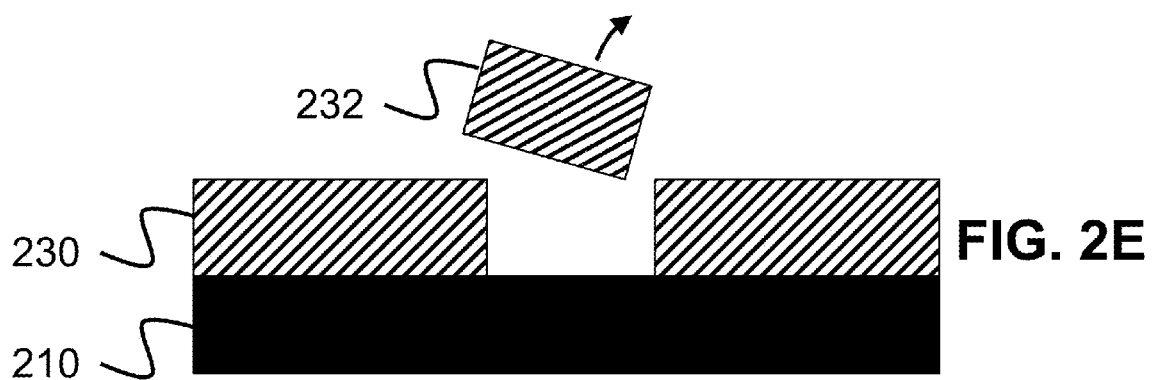
Figure 3:
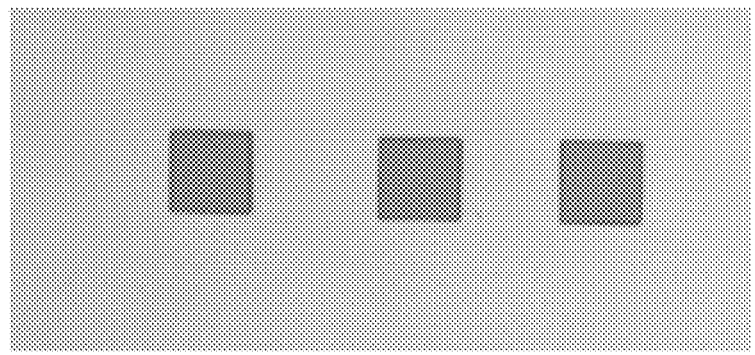
FIG. 3 shows according to an exemplary embodiment of the invention an image of the substrate after the lift-off process. Image (darker squares) showing bare silicon where glass flakes have been lifted off into solution.
Figure 4:
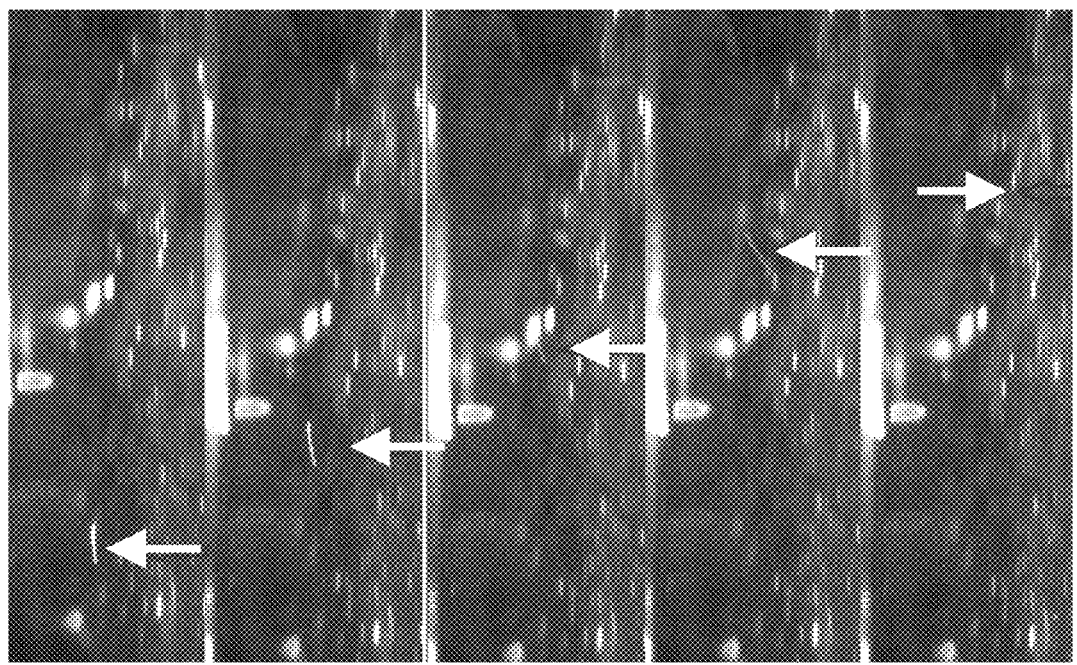
FIG. 4 shows according to an exemplary embodiment of the invention shows a still frame capture of a glass flake in solution. The arrow points to the flake as it moves through the solution.
Figure 5:
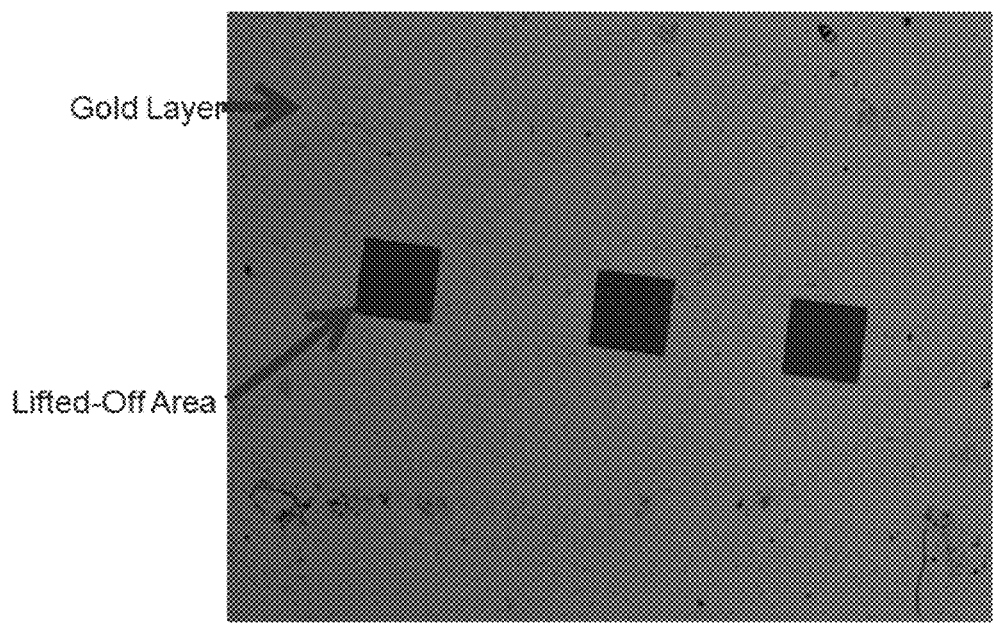
FIG. 5 shows according to an exemplary embodiment of the invention a prototype sample where the lift-off layer is carried out with gold instead of glass to highlight the lift-off.
Figure 6:
FIG. 6 shows according to an exemplary embodiment of the invention a prototype sample where the lift-off layer is gold instead of glass to highlight where the layer has lifted off. This image (using a far-field microscope) shows the substrate still in the vial.

FIGS. 2A-E shows according to the invention the micropatterning method for creating morphologically specific free-floating structures to be used as Standards in the pharmaceutical industry. FIG. 2A shows a clean wafer or substrate 210 that is prepared using piranha etch (a mixture of sulfuric acid and hydrogen peroxide) as well as solvent cleaning with acetone, IPA, DI water and a nitrogen drying step as deemed necessary. The typical hydrofluoric acid etch is not utilized to promote adhesion between the substrate and photoresist layers. FIG. 2B shows a sacrificial layer 220 that is sensitive to UV light and is deposited on a small piece of the substrate that has been scribed from the original wafer. In the example shown the sacrificial layer is 5214E Photoresist as obtained from MicroChem (Santa Clara, Calif.). The layer is spin coated on the sample at 3200 rpm at room temperature for 45 seconds, followed by a hard bake at 110° C. for 60 seconds. FIG. 2C shows the wafer 210 is exposed to ultraviolet light underneath a patterned photomask (not shown) in a Karl-Suss (Erfurt, Germany) mask aligner. Exposure for the example shown is 20 seconds. Samples are then placed in AZ 400K developer as obtained from Microchem to remove areas exposed to UV light and to leave the desired pattern 222 on the substrate 210. FIG. 2D shows the entire wafer 210 coated with the desired material 230, in this case silica glass, via a plasma-enhanced chemical vapor deposition (PECVD) process resulting in a thickness ranging from 80-600 nm. Other deposition methods and materials can be used if required. It should be noted that the thickness of the deposition material should not exceed or approach the thickness of the sacrificial layer as this may cause the layer to remain permanently on the substrate in the patterned areas. FIG. 2E shows the sample placed in solvent, in this case acetone. After the desired flakes lift-off 232 into the vial solution the substrate can be removed and examined. This is to confirm both the number of flakes no longer present (from the number of holes in the substrate) as well as the dimensions of the remaining holes, which will correspond to the dimensions of the glass flakes.

In another embodiment of this invention a shadow mask technique could be utilized to do a direct deposition of material down on the substrate without having to incorporate a photolithography step. This technique could also use the deposition of several different materials to create flake like standards of almost any material. FIGS. 3-6 show different pictures of the samples and the substrate after the process described is carried out.

What is claimed is:

1. A micropatterning method for creating morphologically specific free-floating structures for use as Standards in the pharmaceutical industry to test surface delamination of drug containers, comprising:
    (a) micropatterning morphologically specific free-floating structures with similar characteristics to free-floating structures in a drug product caused by surface delamination of containers holding the drug product, wherein the micropatterning comprises:
        (i) providing a substrate;
        (ii) depositing a layer of UV light sensitive material onto the substrate;
        (iii) exposing the wafer to UV light underneath a photomask with a desired pattern and specific morphologic dimensions defined by the desired pattern to remove areas exposed to the UV light and leaving the desired pattern of the UV light material on the substrate;
        (iv) coating the substrate and the desired pattern of the UV light material left on the substrate with a coating layer wherein the thickness of the coating does not exceed the thickness of the UV light sensitive layer; and
        (v) using a solvent to lift-off structures of the coating layer which are defined by the desired pattern, wherein the lifted-off structures are referred to as standards;
    (b) providing a container filled a defined number of the standards; and
    (c) using the filled container as a standard for testing other drug products held in a drug container (j) made out of a material similar to the coating layer or (jj) having an inner coating similar to the coating layer, wherein the testing pertains to optically identifying structures in the drug container (p) similar in size and shape as the standards, or (pp) different in size and shape as the standards.

2. A micropatterning method for creating morphologically specific free-floating structures for use as Standards in the pharmaceutical industry to test objects in drug containers, comprising:
    (a) micropatterning morphologically specific free-floating structures, wherein the micropatterning comprises:
        (i) providing a substrate;
        (ii) depositing a layer of UV light sensitive material onto the substrate;
        (iii) exposing the wafer to UV light underneath a photomask with a desired pattern and specific morphologic dimensions defined by the desired pattern to remove areas exposed to the UV light and leaving the desired pattern of the UV light material on the substrate;
        (iv) coating the substrate and the desired pattern of the UV light material left on the substrate with a coating layer wherein the thickness of the coating does not exceed the thickness of the UV light sensitive layer; and (v) using a solvent to lift-off structures of the coating layer which are defined by the desired pattern, wherein the lifted-off structures are referred to as standards;

(b) providing a container filled a defined number of the standards; and (c) using the filled container as a standard for testing other drug products held in a drug container, wherein the testing pertains to optically identifying structures in the drug container (j) similar in size and shape as the standards, or (jj) different in size and shape as the standards.

3. A method of using morphologically specific free-floating structures as Standards in the pharmaceutical industry to test objects in drug containers, comprising:

(a) micropatterning morphologically specific free-floating structures defined by a desired pattern, wherein structures are referred to as standards;

(b) providing a container filled a defined number of the standards; and (c) using the filled container as a standard for testing other drug products held in a drug container, wherein the testing pertains to optically identifying structures in the drug container (j) similar in size and shape as the standards, or (jj) different in size and shape as the standards.

* * * * *